(12) United States Patent
Simpson et al.

(10) Patent No.: US 11,406,425 B2
(45) Date of Patent: Aug. 9, 2022

(54) TETHERS FOR USE WITH FASTENER ASSEMBLIES AND METHOD FOR USING TETHERS WITH FASTENER ASSEMBLIES

(71) Applicant: Warsaw Orthopedic, Inc., Warsaw, IN (US)

(72) Inventors: Joshua Simpson, Collierville, TN (US); William Alan Rezach, Covington, TN (US); Charles Anthony Dickinson, Arlington, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 196 days.

(21) Appl. No.: 16/540,559

(22) Filed: Aug. 14, 2019

(65) Prior Publication Data
US 2021/0045777 A1 Feb. 18, 2021

(51) Int. Cl.
*A61B 17/70* (2006.01)
*A61B 17/86* (2006.01)

(52) U.S. Cl.
CPC ...... *A61B 17/7022* (2013.01); *A61B 17/8605* (2013.01); *A61B 17/7035* (2013.01); *A61B 17/7083* (2013.01)

(58) Field of Classification Search
CPC ............ A61B 17/7022; A61B 17/7053; A61B 17/842; A61B 17/7067
See application file for complete search history.

(56) References Cited

U.S. PATENT DOCUMENTS

| 5,306,275 | A | * | 4/1994 | Bryan | A61B 17/7055 |
| | | | | | 606/267 |
| 5,725,582 | A | * | 3/1998 | Bevan | A61B 17/842 |
| | | | | | 623/13.12 |
| 6,248,106 | B1 | * | 6/2001 | Ferree | A61B 17/7022 |
| | | | | | 606/328 |
| 9,707,013 | B2 | | 7/2017 | Rezach et al. | |
| 9,872,711 | B2 | | 1/2018 | Hynes et al. | |
| 9,949,776 | B2 | | 4/2018 | Mobasser et al. | |
| 9,962,171 | B2 | | 5/2018 | Rezach et al. | |
| 9,974,569 | B2 | | 5/2018 | Lehmann, Jr. et al. | |
| 9,993,270 | B2 | | 6/2018 | Butler | |
| 10,028,770 | B2 | | 7/2018 | Rezach et al. | |
| 2005/0143823 | A1 | * | 6/2005 | Boyd | A61B 17/8685 |
| | | | | | 606/279 |
| 2008/0009866 | A1 | * | 1/2008 | Alamin | A61B 17/7053 |
| | | | | | 606/151 |

(Continued)

OTHER PUBLICATIONS

U.S. Appl. No. 15/843,938, filed Dec. 15, 2017 to May et al.
U.S. Appl. No. 16/380,739, filed Apr. 10, 2019 to Rezach et al.

*Primary Examiner* — Julianna N Harvey

(57) ABSTRACT

One or more tethers for use with fastener assemblies and a method for use of the one or more tethers with the fastener assemblies is provided. The one or more tethers can be attached between a first fastener assembly positioned with respect to a first vertebrae adjacent a first side of a spinous process of a second vertebrae and a second fastener assembly positioned with respect to the vertebrae adjacent a second side of the spinous process of the second vertebrae. The one or more tethers can be tensioned against the spinous process of the second vertebrae to mitigate stresses on an uninstrumented level of the spine.

20 Claims, 6 Drawing Sheets

(56) References Cited

U.S. PATENT DOCUMENTS

| | | | |
|---|---|---|---|
| 2009/0270920 A1* | 10/2009 | Douget | A61B 17/7067 606/264 |
| 2010/0106195 A1* | 4/2010 | Serhan | A61B 17/8894 606/279 |
| 2010/0318133 A1* | 12/2010 | Tornier | A61B 17/7067 606/270 |
| 2011/0313465 A1* | 12/2011 | Warren | A61B 17/8685 606/279 |
| 2012/0150231 A1* | 6/2012 | Alamin | A61B 17/7067 606/279 |
| 2013/0072983 A1* | 3/2013 | Lindquist | A61B 17/8869 606/279 |
| 2013/0253587 A1* | 9/2013 | Carls | A61B 17/7022 606/279 |
| 2017/0245898 A1 | 8/2017 | May et al. | |
| 2018/0064469 A1* | 3/2018 | Blakemore | A61B 17/7022 |
| 2018/0078286 A1* | 3/2018 | Le Couëdic | A61B 17/7049 |
| 2019/0290329 A1* | 9/2019 | Bess | A61B 17/7053 |

* cited by examiner

TETHERS FOR USE WITH FASTENER ASSEMBLIES AND METHOD FOR USING TETHERS WITH FASTENER ASSEMBLIES

FIELD

The present technology is generally related to a tethers or tethers used with fastener assemblies and methods for using the tether or tethers with the fastener assemblies.

BACKGROUND

Spinal rods and fastener assemblies can be used in forming a framework on a patient's spine to facilitate correction of issues with spinal deformity (such as scoliosis), tumor, trauma, or degenerative conditions. The spinal rods are interconnected with the fastener assemblies attached directly to vertebrae to form the framework. However, uninstrumented levels of the patient's spine adjacent the instrumented levels of the framework are subjected to significant stresses. Therefore, there is a need for mitigating the stresses on these uninstrumented levels.

SUMMARY

The techniques of this disclosure generally relate to one or more tethers usable with fastener assemblies.

In one aspect, the present disclosure provides a method for stabilizing a portion of a spine using fastener assemblies and one or more tethers, the method including inserting a screw of a first fastener assembly into a first vertebrae adjacent a first side of a spinous process of the first vertebrae; inserting a screw of a second fastener assembly into the first vertebrae adjacent a second side of the spinous process of the vertebrae; attaching a first end portion of a tether to the screw of the first fastener assembly; extending a length of the tether over a portion of a spinous process of a second vertebrae above the first vertebrae at an uninstrumented level of the spine; attaching a second end portion of the tether to the screw of the second fastener assembly; and tensioning the tether over the spinous process of the second vertebrae relative to the screws of the first and second fastener assemblies.

In another aspect, the disclosure provides a method for stabilizing a portion of a spine using fastener assemblies and one or more tethers, the method including attaching a first end portion of a tether to a screw of a first fastener assembly attached to a first vertebrae of an instrumented level on a first side of a sagittal plane; extending a length of the tether over a portion of a spinous process of a second vertebrae above the first vertebrae at an uninstrumented level of the spine; attaching a second end portion of the tether to a screw of a second fastener assembly attached to the first vertebrae of the instrumented level on a second side of the sagittal plane; and tensioning the tether over the spinous process of the second vertebrae relative to the screws of the first and second fastener assemblies.

In yet another aspect, the disclosure provides a method for stabilizing a portion of a spine using fastener assemblies and one or more tethers, the method including attaching a first end portion of a tether to a screw of a first fastener assembly attached to a first vertebrae of an instrumented level on a first side of a sagittal plane; extending a length of the tether over a portion of a spinous process of a second vertebrae above the first vertebrae at an uninstrumented level of the spine; attaching a second end portion of the tether to a screw of a second fastener assembly attached to the first vertebrae of the instrumented level on a second side of the sagittal plane; tensioning the tether over the spinous process of the second vertebrae; attaching a receiver of the first fastener assembly over a head portion of the screw of the first fastener assembly after attaching the first end portion of the tether to the screw of the first fastener assembly; and attaching a receiver of the second fastener assembly over a head portion of the screw of the second fastener assembly after attaching the second end portion of the tether to the screw of the second fastener assembly.

The details of one or more aspects of the disclosure as set forth in the accompanying drawings and the description below. Other features, objects, and advantages of the techniques described in this disclosure will be apparent from the description and drawings, and from the claims.

DETAILED DESCRIPTION

Figure 1:
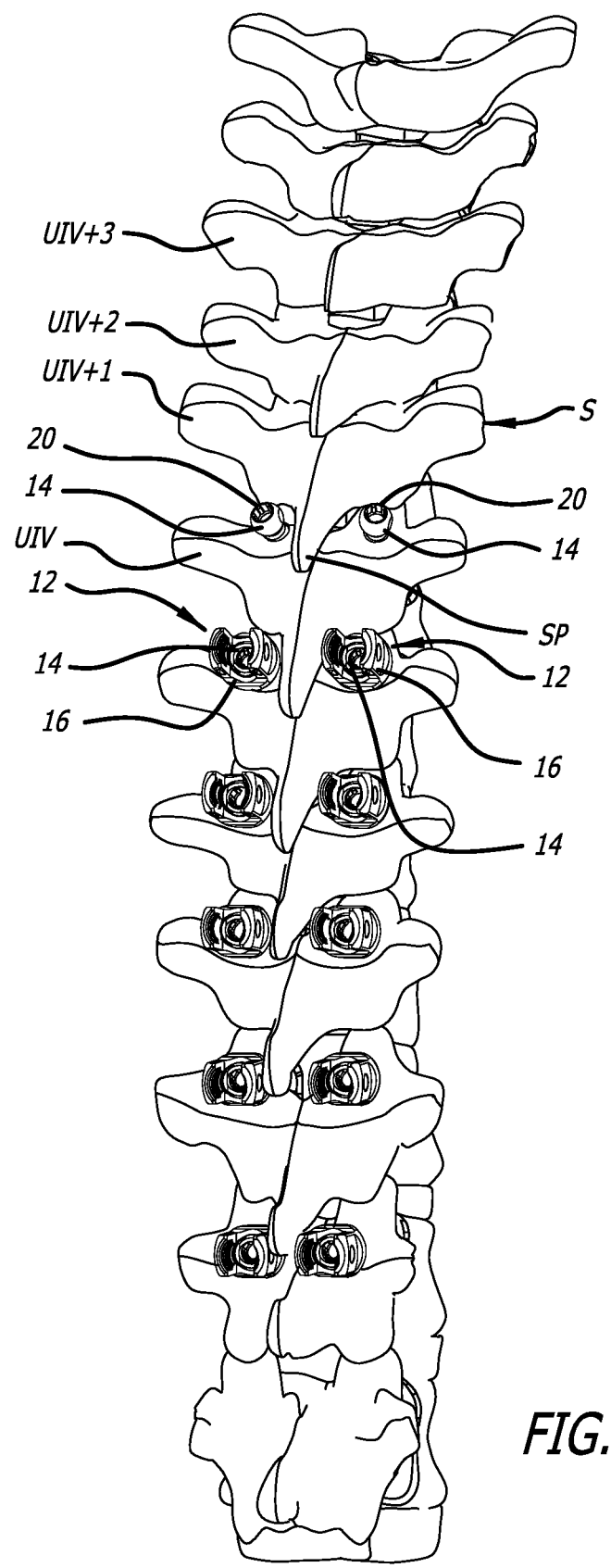
FIG. 1 is a rear, perspective view that illustrates various fastener assemblies received in instrumented levels of a patient's spine.
Figure 2:
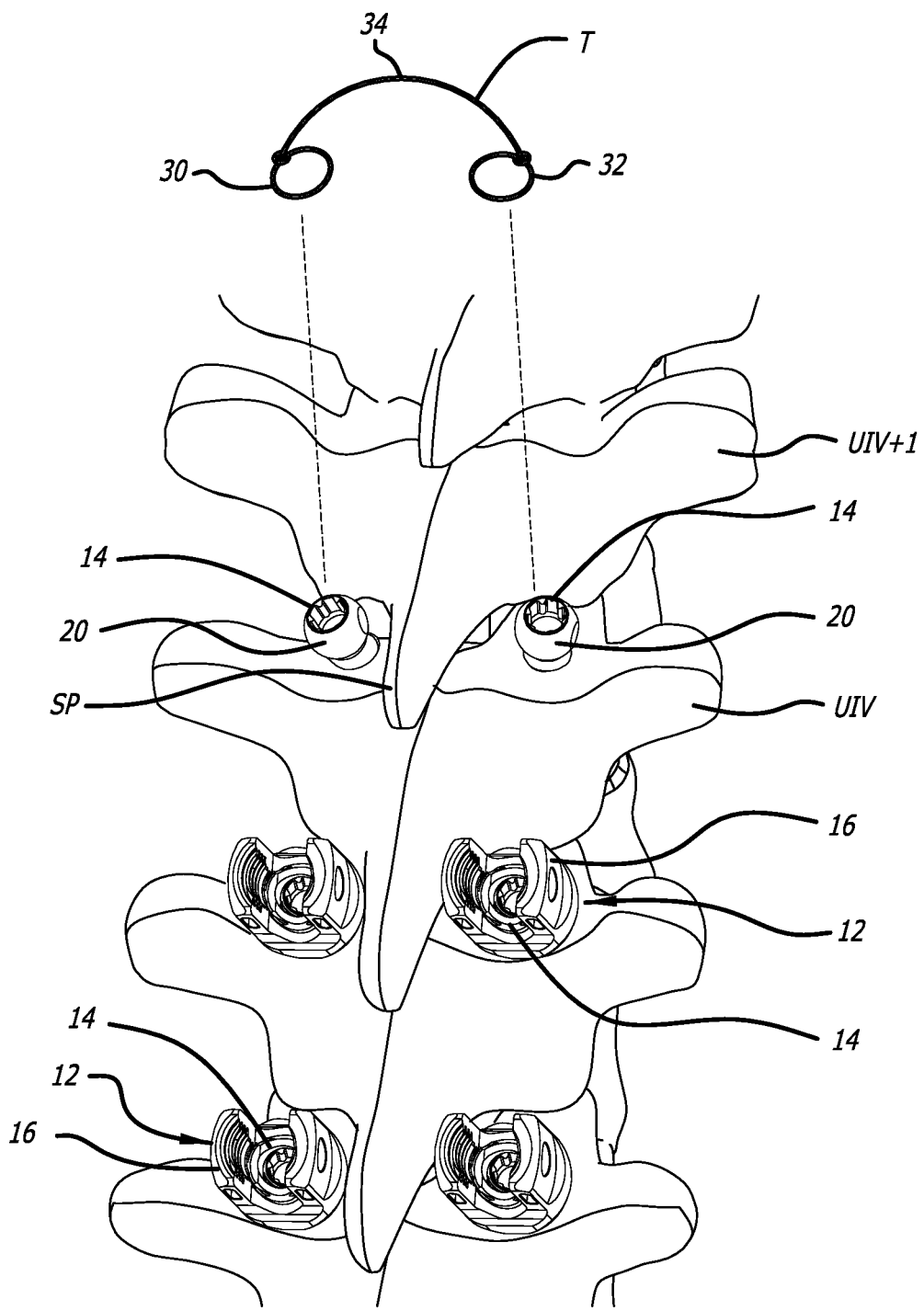
FIG. 2 is an enlarged, rear, perspective view that illustrates various fastener assemblies received in instrumented levels of a patient's spine and placement of an embodiment of a tether with respect to an upper instrumented level of the patient's spine.
Figure 3:
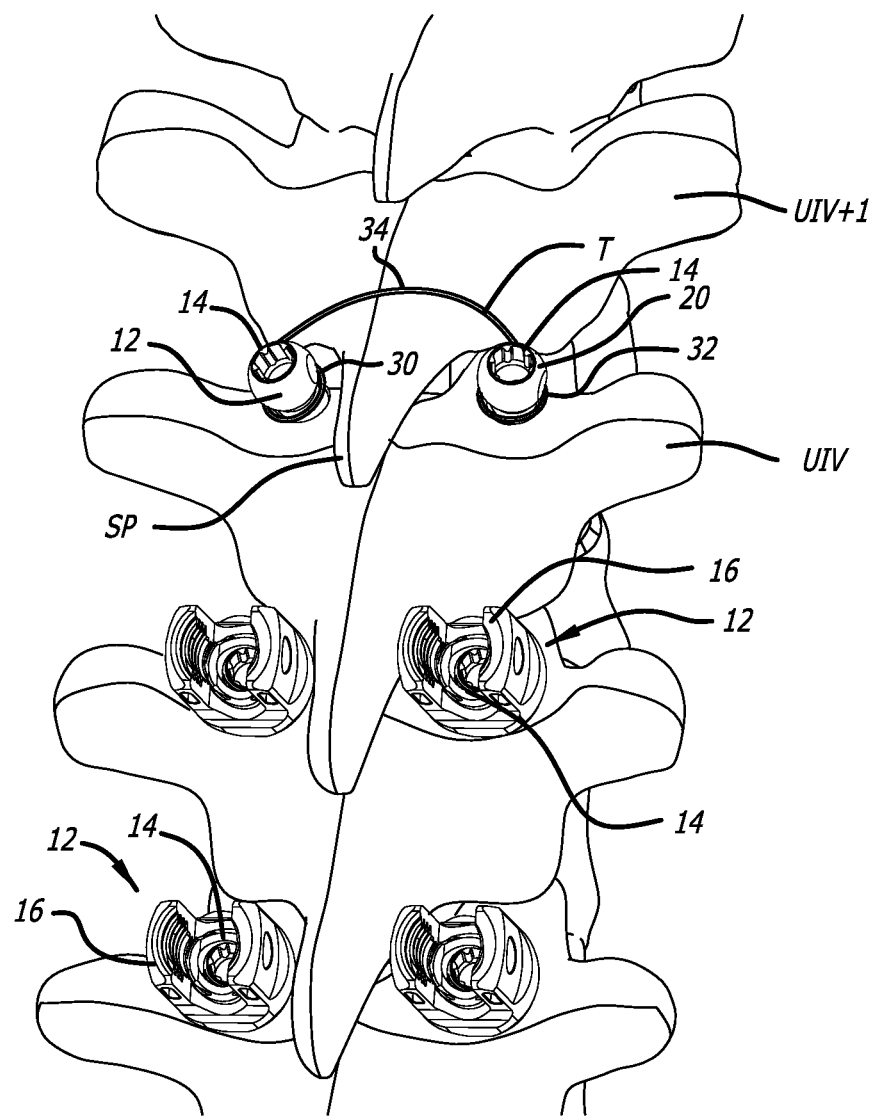
FIG. 3 is an enlarged, rear, perspective view that illustrates attachment of the tether of FIG. 2 to screws of the fastener assemblies of the upper instrumented level of the patient's spine.
Figure 4:
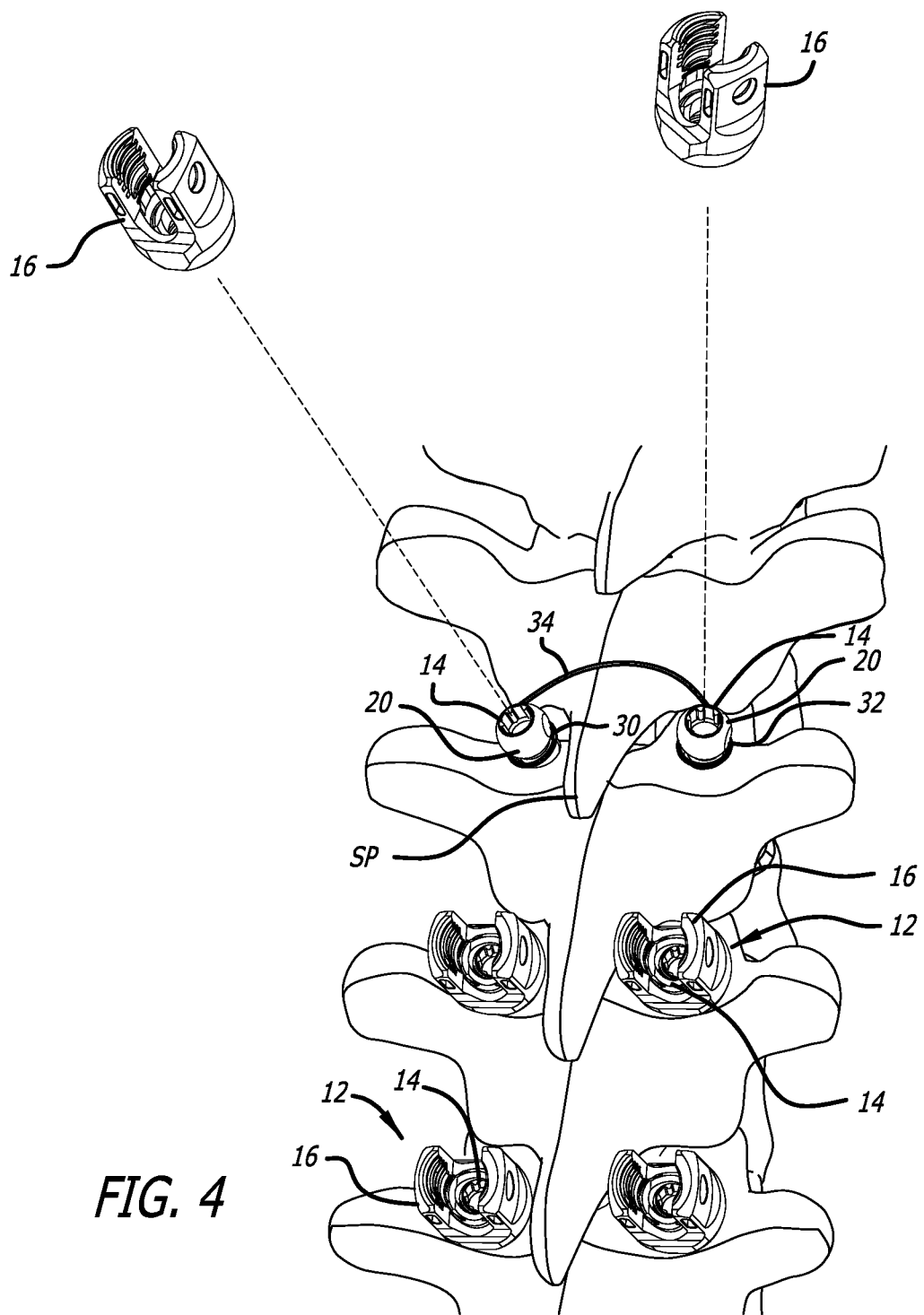
FIG. 4 is an enlarged, rear, perspective view that illustrates attachment of receivers to screws of the fastener assemblies of the upper instrumented level of the patient's spine to hold the tether of FIGS. 2 and 3 in place.
Figure 5:
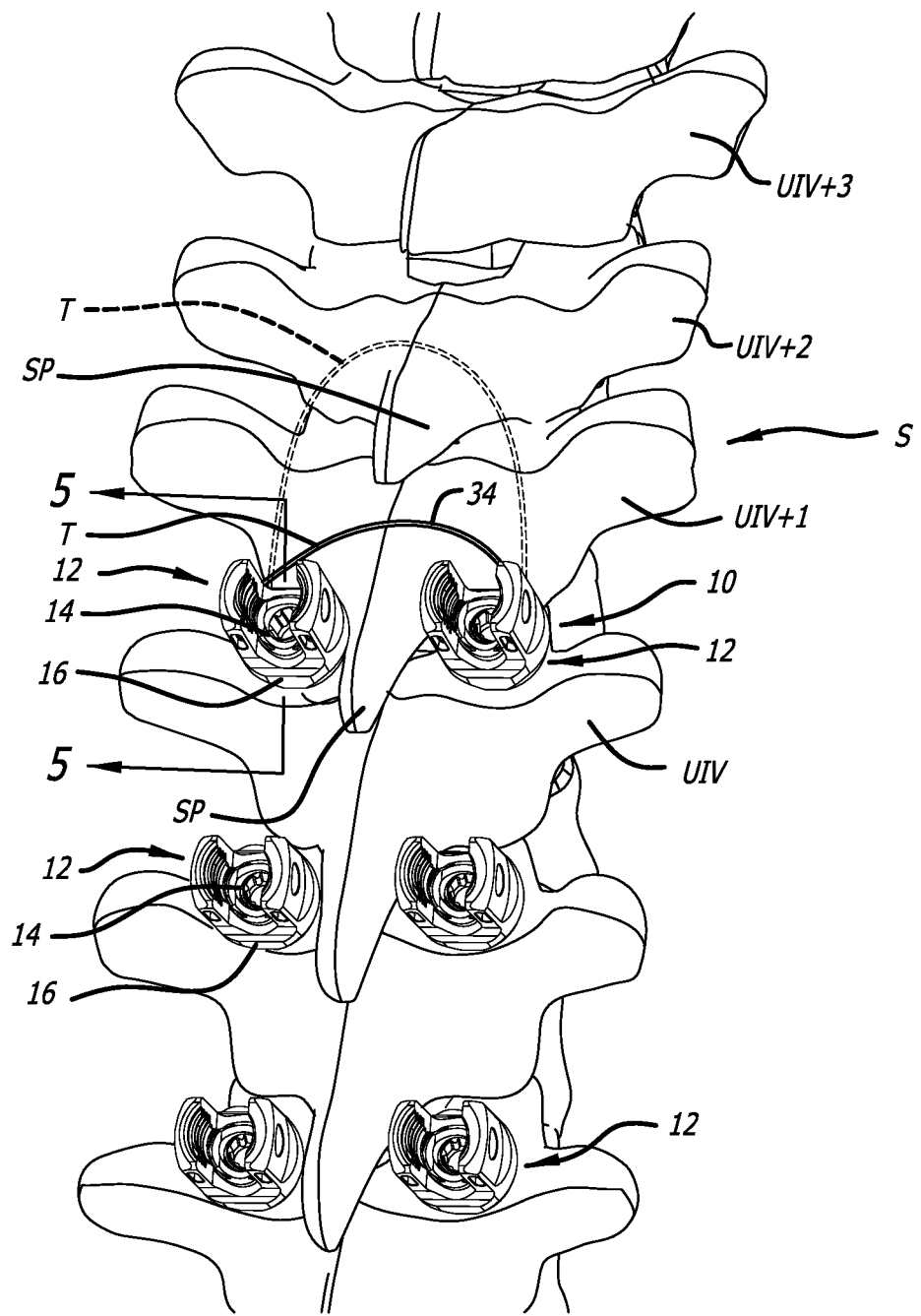
FIG. 5 is an enlarged, rear, perspective view that illustrates the tether of FIGS. 2-4 and another tether attached to the fastener assemblies of the upper instrumented level of the patient's spine.

A construct according to a preferred embodiment of the present disclosure is generally indicated by the numeral 10 in FIG. 5. The construct 10 can be formed as an intermediate step in constructing a final framework with respect to a patient's spine S. The final framework can be used in stabilizing the spine S to correct issues with spinal deformity (such as scoliosis), tumor, trauma, or degenerative conditions.

The construct 10 is formed from at least two fastener assemblies 12 and one or more tethers T positioned with respect to vertebrae of the patient's spine S. As discussed below, the one or more tethers T can be used in mitigating stresses on vertebrae adjacent to the final framework by stabilizing these adjacent vertebrae. Also, the one or more tethers T can be used in creating desirable tension between the final framework and the vertebrae adjacent to the first framework for therapeutic purposes. The fastener assemblies 12 can be identical or similar to fastener assemblies disclosed in U.S. Ser. Nos. 15/843,938 and 16/380,739, which are herein incorporated by reference in their entirety. As disclosed in Ser. No. 16/380,739, for example, the fastener assemblies 12 can include a screw 14, a receiver 16, a crown C, a first expansion (or retaining) ring $R_1$, a second expansion (or retaining) ring $R_2$.

The levels of the patient's spine S at which the final framework is formed are called instrumented levels. An upper instrumented level (UIV), various instrumented levels below the UIV, and uninstrumented levels UIV+1, UIV+2, and UIV+3 above the UIV are depicted in FIGS. 1-5. To form the final framework, the screws 14, as depicted in FIGS. 1-5, are positioned in pedicles on opposite sides of a sagittal plane of the patient at multiple instrumented levels (including the UIV) of the patient's spine S.

Figure 6:
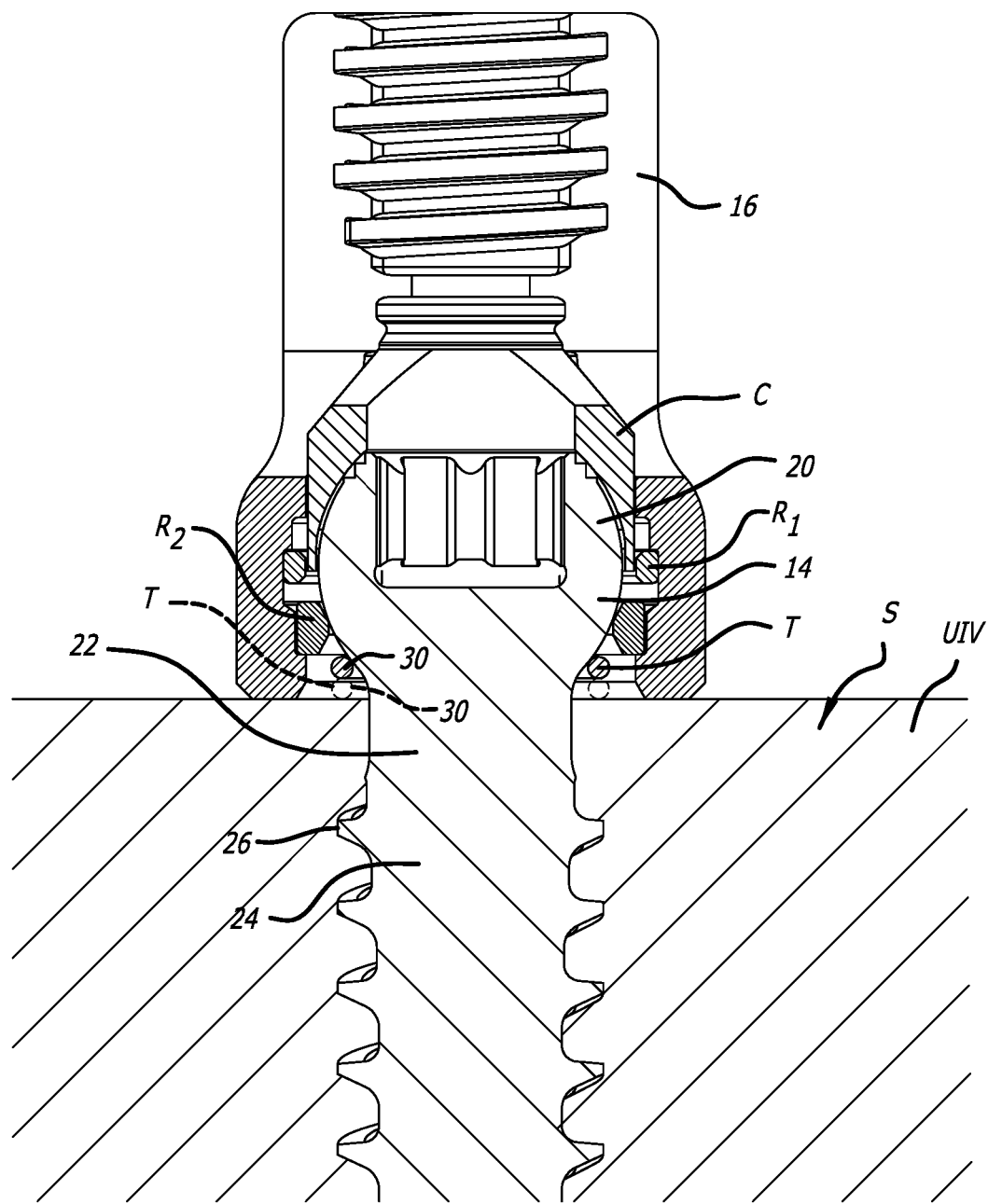
FIG. 6 is a cross-sectional view taken along Line 5-5 showing the tethers of FIG. 5 attached to one of the fastener assemblies of the upper instrumented level.

For each of the fastener assemblies 12, as depicted in FIG. 6 the receiver 16 is positioned on the screw 14, and the crown C, first expansion ring $R_1$, and second expansion ring $R_2$ are used in retaining the receivers 16 on the screws 14 while affording pivotal and rotational adjustment. Portions of spinal rods (not shown) can then be positioned in each of the receivers 16, and threaded covers (not shown) can be engaged to the receivers 16 to retain the portions of the spinal rods within the receivers to facilitate interconnection of the spinal rods between the fastener assemblies 12. Furthermore, the engagement of the threaded covers to the receivers 16, and the corresponding interaction of the spinal rods, crowns C, first expansion rings $R_1$, and second expansion rings $R_2$ with respect to the screws 14 can be used to hold the pivotal and rotational position of the receivers 16 relative to the screws 14.

Before completing formation of the final framework, one or more of the tethers T, as depicted in FIGS. 2-5, can be secured between screws 14 on opposite sides of the sagittal plane of the patient at an instrumented level of the patient's spine S. The one or more tethers T are used in stabilizing the uninstrumented levels adjacent the final framework. Typically, uninstrumented levels of the patient's spine adjacent the instrumented levels of the final framework are subjected to significant stresses, and the one or more of the tethers T can be used to mitigate the stresses on these uninstrumented levels. Furthermore, the one or more tethers T can also be used to create desirable tension between the final framework and the uninstrumented levels of the patient's spine adjacent the instrumented levels of the final framework for therapeutic purposes by applying a desirable force or forces to the uninstrumented levels of the patient's spine.

As depicted in FIGS. 1-5, a spinous process SP of the UIV+1 extends downwardly from the UIV+1 between the screws 14 positioned in the UIV on either side of the sagittal plane. The tether T can be secured to the screw 14 received in the UIV on the left side of the spinous process SP of the UIV+1 and secured to the screw 14 received in the UIV on the right side of the spinous process SP of the UIV+1, and the tether T be positioned over the spinous process SP of UIV+1 between the screws 14 of the UIV. The connection between the final framework and the UIV+1 serves in stabilizing the UIV+1 relative to the final framework to mitigate the stresses on the uninstrumented levels, and/or create desirable tension.

The placement of the tether T, however, is not limited to between the screws 14 of the UIV and over the spinous process SP of the UIV+1. Alternative and/or additional tethers T can be provided to stabilize the vertebrae adjacent the final framework. These tethers T can extend between the screws 14 of any of the instrumented levels and over the spinous processes of UIV+1, UIV+2, UIV+3, etc. The placement of the tether T and/or use of multiple tethers can further mitigate the stresses on the uninstrumented levels, and/or further create desirable tension. For example, another tether T (indicated by dashed lines in FIG. 5) can be used, and can extend between the screws 14 of the UIV and over the spinous process SP of the UIV+2. Furthermore, other tethers T (used by the or with the tethers T of FIGS. 1-5) can extend between the screws 14 of one of the instrumented levels below the UIV and over the spinous processes of one of the UIV+1, UIV+2, UIV+3, etc.

As depicted in FIG. 6, each of the screws 14 can include a head portion 20, a neck portion 22, and a shaft portion 24. The shafts 24 of each of the screws 14, as depicted in FIG. 6, can include one or more threadforms 26 facilitating attachment of the screws 14 to the vertebrae. The one or more tethers T can be secured to the head portions 20 and/or the neck portions 22 below the head portions 20 of the screws 14. To illustrate, the tether T, as depicted in FIGS. 2-5, includes a first end portion 30, a second end portion 32, and a length 34 between the first end portion 30 and the second end portion 32. After the screws 14 have been positioned, the first end portion 30 of the tether T can be secured to the head portion 20 and/or the neck portion 22 of one of the screws 14 on one side of the sagittal plane, and then the second end portion 32 of the tether T can be secured to the head portion 20 and/or the neck portion 22 of the other of the screws 14 on the other side of the sagittal plane.

The securing of the tether T to the respective screws 14 can be effectuated via attachment of the tether T to the screws 14 using knots, fasteners, adhesives, or a combination of knots, fasteners, and/or adhesives. Furthermore, the attachment process can serve to add tension to the tether T. For example, as depicted in FIGS. 2-5, the first end portion 30 of the tether T could be knotted to one of the screws 14, and then the second end portion 32 of the tether T could be knotted to the other of the screws 14, and during the knotting process, the tether T could be pulled tight against the spinous process SP located between the screws 14. The knots of the first end portion 30 and the second end portion 32 can be preformed or be formed during attachment of the tether T to the screws 14. The tension in the tether T can also be increased by using a tether T having elastic properties and/or incorporating ratcheting as part of the fasteners.

While the tether T, as depicted in FIGS. 2-5, has a uniform diameter, the tether T can have variable diameters along its length. To illustrate, the tether T could have relatively small widths at the first end portion 30 and the second end portion 32, and have a relatively large width along its length between the first end portion 30 and the second end 32. The larger width along the length of the tether T between the first end 30 and the second end 32 can be used in aiding the application of tension to the spinous process SP.

After the first end portion 30 and the second end portion 32 of the tether T are attached to the respective screws 14, the receivers 16 can be placed over the head portions 20 of the screws 14. As depicted in FIG. 6, the placement of the receivers 16 over the head portions 20 can be used to prevent detachment of the first end portion 30 and the second end portion 32 of the tether T from the respective screws 14. The receivers 16 can prevent the first end portion 30 and the second end portion 32 from slipping over the head portions 20 of the respective screws 14, and, if received over the first end portion 30 and the second end portion 32, the receivers 16 can be used in clamping the tether T to the respective screws 14. After the construct 10 is formed from the at least two fastener assemblies 12 and one or more tethers T, the final framework can be constructed by attaching spinal rods between the fastener assemblies 12 by positioning portions of the spinal rods in each of the receivers 16, and engaging threaded covers to retain the portions of the spinal rods within the receivers 16.

It should be understood that various aspects disclosed herein may be combined in different combinations than the combinations specifically presented in the description and the accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method for stabilizing a portion of a spine using fastener assemblies and one or more tethers, the method comprising:
    inserting a screw of a first fastener assembly into a first vertebra adjacent a first side of a spinous process of the first vertebra, the screw of the first fastener assembly including a head portion;
    inserting a screw of a second fastener assembly into the first vertebra adjacent a second side of the spinous process of the first vertebra, the screw of the second fastener assembly including a head portion;
    attaching a first end portion of a tether relative to the head portion of the screw of the first fastener assembly;
    extending a length of the tether over a portion of a spinous process of a second vertebra above the first vertebra at an uninstrumented level of the spine;
    attaching a second end portion of the tether relative to the head portion of the screw of the second fastener assembly;
    tensioning the tether over the spinous process of the second vertebra relative to the screws of the first and second fastener assemblies;
    attaching a receiver of the first fastener assembly over the head portion of the screw of the first fastener assembly so that a distal portion of the receiver of the first fastener assembly contacts a first surface of the first vertebra;
    attaching a receiver of the second fastener assembly over the head portion of the screw of the second fastener assembly so that a distal portion of the receiver of the second fastener assembly contacts a second surface of the first vertebra;
    wherein the first end portion of the tether is enclosed within an area formed by the first surface of the first vertebra, the receiver of the first fastener assembly, and the head portion of the first fastener assembly; and
    wherein the second end portion of the tether is enclosed within an area formed by the second surface of the first vertebra, the receiver of the second fastener assembly, and the head portion of the second fastener assembly.

2. The method of claim 1, wherein the first end portion of the tether is positioned between a retaining ring of the receiver of the first fastener assembly and the first surface of the first vertebra.

3. The method of claim 2, wherein the second end portion of the tether is positioned between a retaining ring of the receiver of the second fastener assembly and the second surface of the first vertebra.

4. The method of claim 1, wherein attaching the first end portion of the tether comprises knotting the first end portion to a shaft portion and/or the head portion of the screw of the first fastener assembly.

5. The method of claim 4, wherein attaching the second end portion of the tether comprises knotting the second end portion to a shaft portion and/or the head portion of the screw of the second fastener assembly.

6. The method of claim 1, wherein attaching the first end portion relative to the head portion of the screw of the first fastener assembly is effectuated using at least one of a knot, a fastener, an adhesive, or a combination of a knot, a fastener, and/or an adhesive, and attaching the second end portion relative to the head portion of the screw of the second fastener assembly is effectuated using at least one of a knot, a fastener, an adhesive, or a combination of a knot, a fastener, and/or an adhesive.

7. The method of claim 6, wherein the first end portion of the tether is positioned between a retaining ring of the receiver of the first fastener assembly and the first surface of the first vertebra.

8. The method of claim 7, wherein the second end portion of the tether is positioned between a retaining ring of the receiver of the second fastener assembly and the second surface of the first vertebra.

9. The method of claim 1, wherein the tether is a first tether and the uninstrumented level is a first uninstrumented level, and the method further comprises:
    before attaching the receiver of the first fastener assembly to the screw of the first fastener assembly, attaching a first end portion of a second tether to the screw of the first fastener assembly;
    extending a length of the second tether over a portion of a spinous process of a third vertebra above the second vertebra at a second uninstrumented level of the spine;
    before attaching the receiver of the second fastener assembly to the screw of the second fastener assembly, attaching a second end portion of the second tether to the screw of the second fastener assembly; and
    tensioning the second tether over the spinous process of the third vertebra relative to the screws of the first and second fastener assemblies;
    wherein the first end portion of the second tether is also enclosed within the area formed by the first surface of the first vertebra, the receiver of the first fastener assembly, and the head portion of the first fastener assembly; and
    wherein the second end portion of the second tether is also enclosed within the area formed by the second surface of the first vertebra, the receiver of the second fastener assembly, and the head portion of the second fastener assembly.

10. A method for stabilizing a portion of a spine using fastener assemblies and one or more tethers, the method comprising:
    attaching a first end portion of a tether to a screw of a first fastener assembly attached to a first vertebra of an instrumented level on a first side of a sagittal plane, the screw of the first fastener assembly having a shaft portion inserted into the first vertebra and a head portion;
    extending a length of the tether over a portion of a spinous process of a second vertebra above the first vertebra at an uninstrumented level of the spine;
    attaching a second end portion of the tether to a screw of a second fastener assembly attached to the first vertebra of the instrumented level on a second side of the sagittal plane, the screw of the second fastener assembly having a shaft portion inserted into the first vertebra and a head portion; and tensioning the tether over the spinous process of the second vertebra relative to the screws of the first and second fastener assemblies, attaching a receiver of the first fastener assembly over the head portion of the screw of the first fastener assembly so that a distal portion of the receiver of the first fastener assembly contacts a first surface of the first vertebra;

attaching a receiver of the second fastener assembly over the head portion of the screw of the second fastener assembly so that a distal portion of the receiver of the second fastener assembly contacts a second surface of the first vertebra;

wherein the first end portion of the tether is enclosed within an area formed by the first surface of the first vertebra, the receiver of the first fastener assembly, and the head portion of the first fastener assembly; and wherein the second end portion of the tether is enclosed within an area formed by the second surface of the first vertebra, the receiver of the second fastener assembly, and the head portion of the second fastener assembly.

11. The method of claim 10, wherein the first end portion of the tether is positioned between a retaining ring of the receiver of the first fastener assembly and the first surface of the first vertebra.

12. The method of claim 11, wherein the second end portion of the tether is positioned between a retaining ring of the receiver of the second fastener assembly and the second surface of the first vertebra.

13. The method of claim 12, wherein the tether is a first tether and the uninstrumented level is a first uninstrumented level, and the method further comprises:

before attaching the receiver of the first fastener assembly to the screw of the first fastener assembly, attaching a first end portion of a second tether to the screw of the first fastener assembly;

extending a length of the second tether over a portion of a spinous process of a third vertebra above the second vertebra at a second uninstrumented level of the spine;

before attaching the receiver of the second fastener assembly to the screw of the second fastener assembly, attaching a second end portion of the second tether to the screw of the second fastener assembly; and tensioning the second tether over the spinous process of the third vertebra relative to the screws of the first and second fastener assemblies;

wherein the first end portion of the second tether is also enclosed within the area formed by the first surface of the first vertebra, the receiver of the first fastener assembly, and the head portion of the first fastener assembly; and wherein the second end portion of the second tether is also enclosed within the area formed by the second surface of the first vertebra, the receiver of the second fastener assembly, and the head portion of the second fastener assembly.

14. The method of claim 10, wherein attaching the first end portion to the screw of the first fastener assembly is effectuated using at least one of a knot, a fastener, an adhesive, or a combination of a knot, a fastener, and/or an adhesive, and attaching the second end portion to the screw of the second fastener assembly is effectuated using at least one of a knot, a fastener, an adhesive, or a combination of a knot, a fastener, and/or an adhesive.

15. A method for stabilizing a portion of a spine using fastener assemblies and one or more tethers, the method comprising:

attaching a screw of a first fastener assembly to a first vertebra of an instrumented level adjacent a first side of a spinous process of the first vertebra so that a head portion of the screw of the first fastener assembly is positioned adjacent a first surface of the first vertebra;

attaching a first end portion of a tether to the screw of the first fastener assembly attached to the first vertebra;

extending a length of the tether over a portion of a spinous process of a second vertebra above the first vertebra at an uninstrumented level of the spine;

attaching a screw of a second fastener assembly to the first vertebra of the instrumented level adjacent a second side of the spinous process of the first vertebra so that a head portion of the screw of the second fastener assembly is positioned adjacent a second surface of the first vertebra;

attaching a second end portion of the tether to the screw of the second fastener assembly attached to the first vertebra;

tensioning the tether over the spinous process of the second vertebra;

attaching a receiver of the first fastener assembly over the head portion of the screw of the first fastener assembly so that a distal portion of the receiver of the first fastener assembly contacts the first surface of the first vertebra; and attaching a receiver of the second fastener assembly over the head portion of the screw of the second fastener assembly so that a distal portion of the receiver of the second fastener assembly contacts the second surface of the first vertebra;

wherein the first end portion of the tether is enclosed within an area formed by the first surface of the first vertebra, the receiver of the first fastener assembly, and the head portion of the first fastener assembly;

wherein the second end portion of the tether is enclosed within an area formed by the second surface of the first vertebra, the receiver of the second fastener assembly, and the head portion of the second fastener assembly; and wherein the first end portion of the tether is positioned between a retaining ring of the receiver of the first fastener assembly and the first surface of the first vertebra, and the second end portion of the tether is positioned between a retaining ring of the receiver of the second fastener assembly and the second surface of the first vertebra.

16. The method of claim 15, wherein attaching the first end portion to the screw of the first fastener assembly is effectuated using knots, fasteners, adhesives, or a combination of knots, fasteners, and/or adhesives.

17. The method of claim 16, wherein attaching the second end portion to the screw of the second fastener assembly is effectuated using knots, fasteners, adhesives, or a combination of knots, fasteners, and/or adhesives.

18. The method of claim 15, wherein the tether is a first tether and the uninstrumented level is a first uninstrumented level, and the method further comprises:

before attaching the receiver of the head portion of the screw of the first fastener assembly, attaching a first end portion of a second tether to the screw of the first fastener assembly;

extending a length of the second tether over a portion of a spinous process of a third vertebra above the second vertebra at a second uninstrumented level of the spine;

before attaching the receiver of the head portion of the screw of the second fastener assembly, attaching a second end portion of the second tether to the screw of the second fastener assembly; and tensioning the second tether over the spinous process of the third vertebra relative to the screws of the first and second fastener assemblies;

wherein the first end portion of the second tether is also enclosed within the area formed by the first surface of the first vertebra, the receiver of the first fastener assembly, and the head portion of the first fastener assembly; and wherein the second end portion of the second tether is also enclosed within the area formed by the second surface of the first vertebra, the receiver of the second fastener assembly, and the head portion of the second fastener assembly.

19. The method of claim 18, wherein attaching the first end portion of the first tether to the screw of the first fastener assembly is effectuated using knots, fasteners, adhesives, or a combination of knots, fasteners, and/or adhesives.

20. The method of claim 19, wherein attaching the second end portion of the first tether to the screw of the second fastener assembly is effectuated using knots, fasteners, adhesives, or a combination of knots, fasteners, and/or adhesives.

* * * * *